United States Patent [19]
Edwards et al.

[11] Patent Number: 5,078,705
[45] Date of Patent: Jan. 7, 1992

[54] DRAIN BAG APPARATUS

[75] Inventors: Forest D. Edwards; Danny L. Hardwick; Li Yuan, all of Salt Lake City, Utah

[73] Assignee: Diasonics, Inc., Milpitas, Calif.

[21] Appl. No.: 651,275

[22] Filed: Feb. 5, 1991

[51] Int. Cl.$^5$ ............................................. A61M 1/00
[52] U.S. Cl. ...................................... 604/322; 604/356
[58] Field of Search .............................. 604/322, 356; 108/25–29, 31, 33–34, 39, 40, 41; 248/99–101; 5/67, 68, 81 R

[56] References Cited

U.S. PATENT DOCUMENTS

| | | |
|---|---|---|
| 1,653,393 | 12/1927 | Cox . |
| 2,149,042 | 2/1939 | Branthover . |
| 3,260,488 | 7/1966 | Kliewer et al. . |
| 3,386,444 | 6/1968 | Brenner et al. . |
| 4,007,741 | 2/1977 | Waldrop et al. . |
| 4,179,159 | 12/1979 | Sieklucki et al. . |
| 4,287,422 | 9/1981 | Kuphal et al. . |
| 4,936,836 | 6/1990 | Weickgenannt . |

OTHER PUBLICATIONS

UROSKOP B 2 Urological X-ray examination table; 10 pages.

*Primary Examiner*—Randy C. Shay
*Assistant Examiner*—A. Paul Zuttarelli
*Attorney, Agent, or Firm*—Blakely, Sokoloff, Taylor & Zafman

[57] ABSTRACT

A drain bag support assembly that is non-removably coupled to a diagnostic urology table, which allows attachment of a drain pan assembly without removal of the drain bag support assembly. The assembly utilizes a shock mechanism and a locking mechanism to allow the urologist to modify the length of the drain bag assembly to fit their particular needs.

The shock mechanism provides for dynamically shortening the length of the assembly by exerting horizontal pressure, while retaining horizontal rigidity. The locking mechanism provides for fixing the assembly to a desired length. The assembly can be placed in a fully closed configuratin and stored underneath the diagnostic urology table. The assembly may also be placed in an extended configuration whereby a drain pan may be attached.

15 Claims, 4 Drawing Sheets

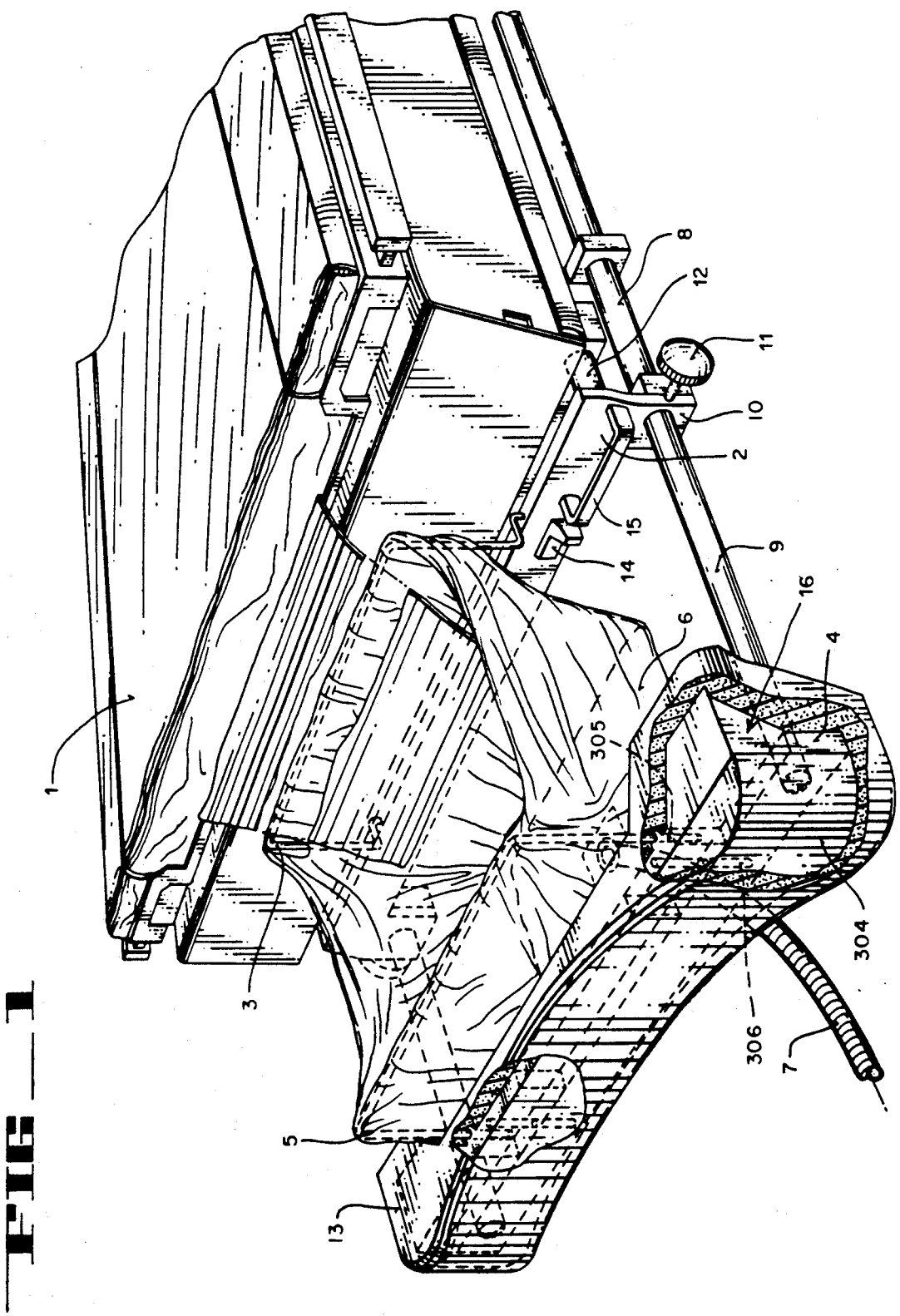

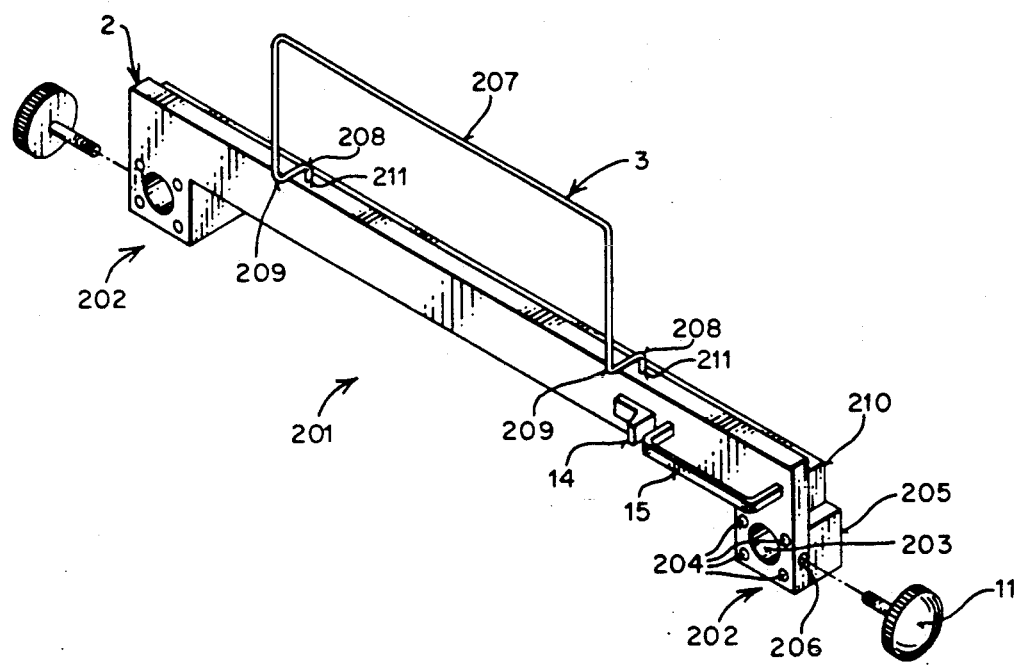
FIG_2A
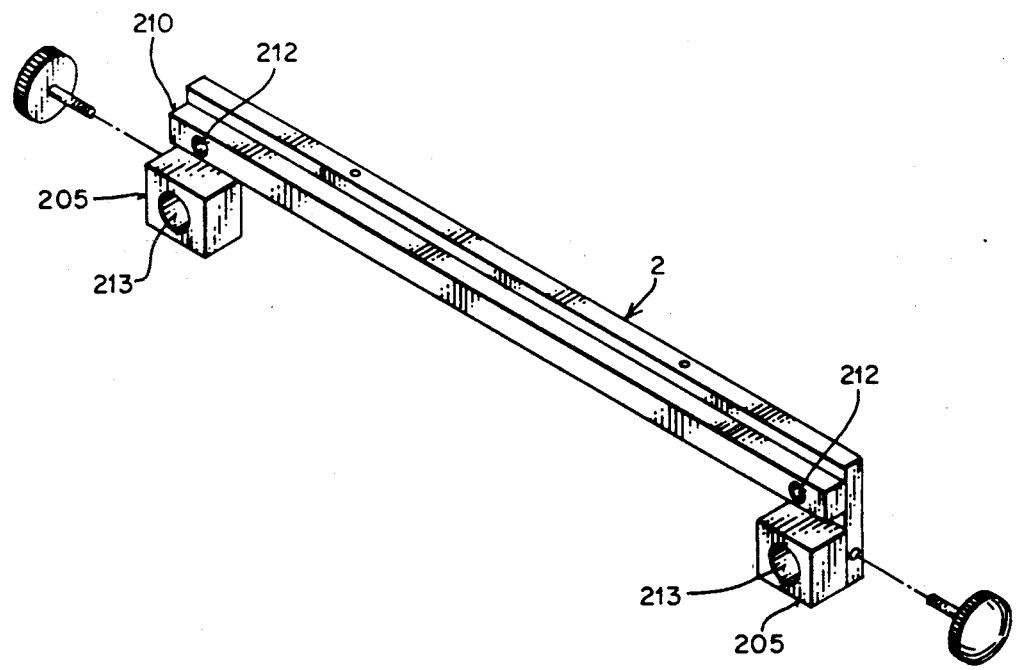
FIG_2B

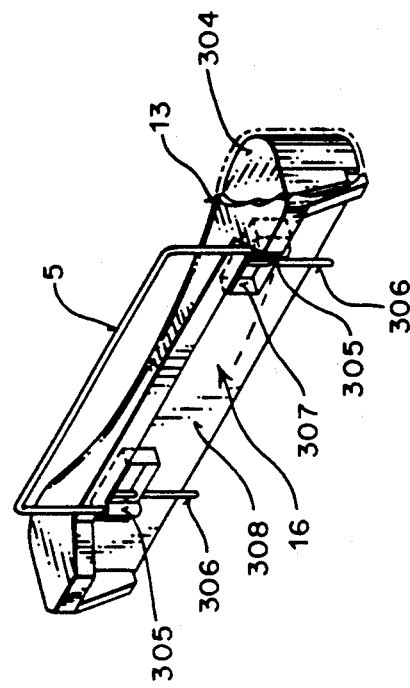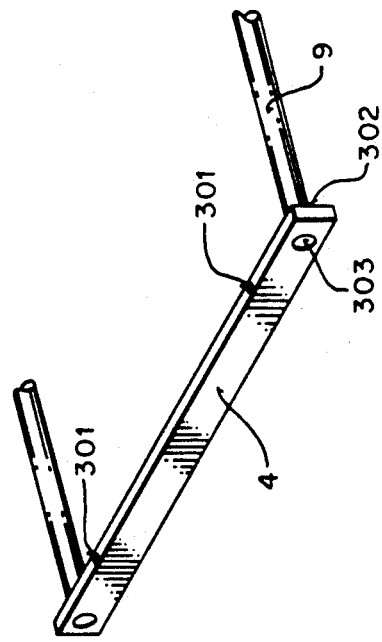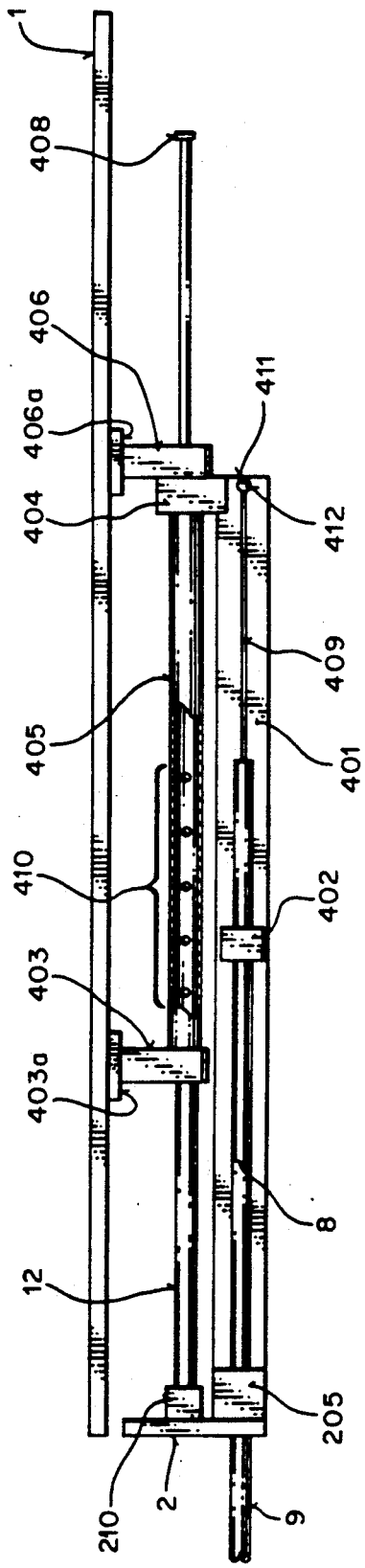

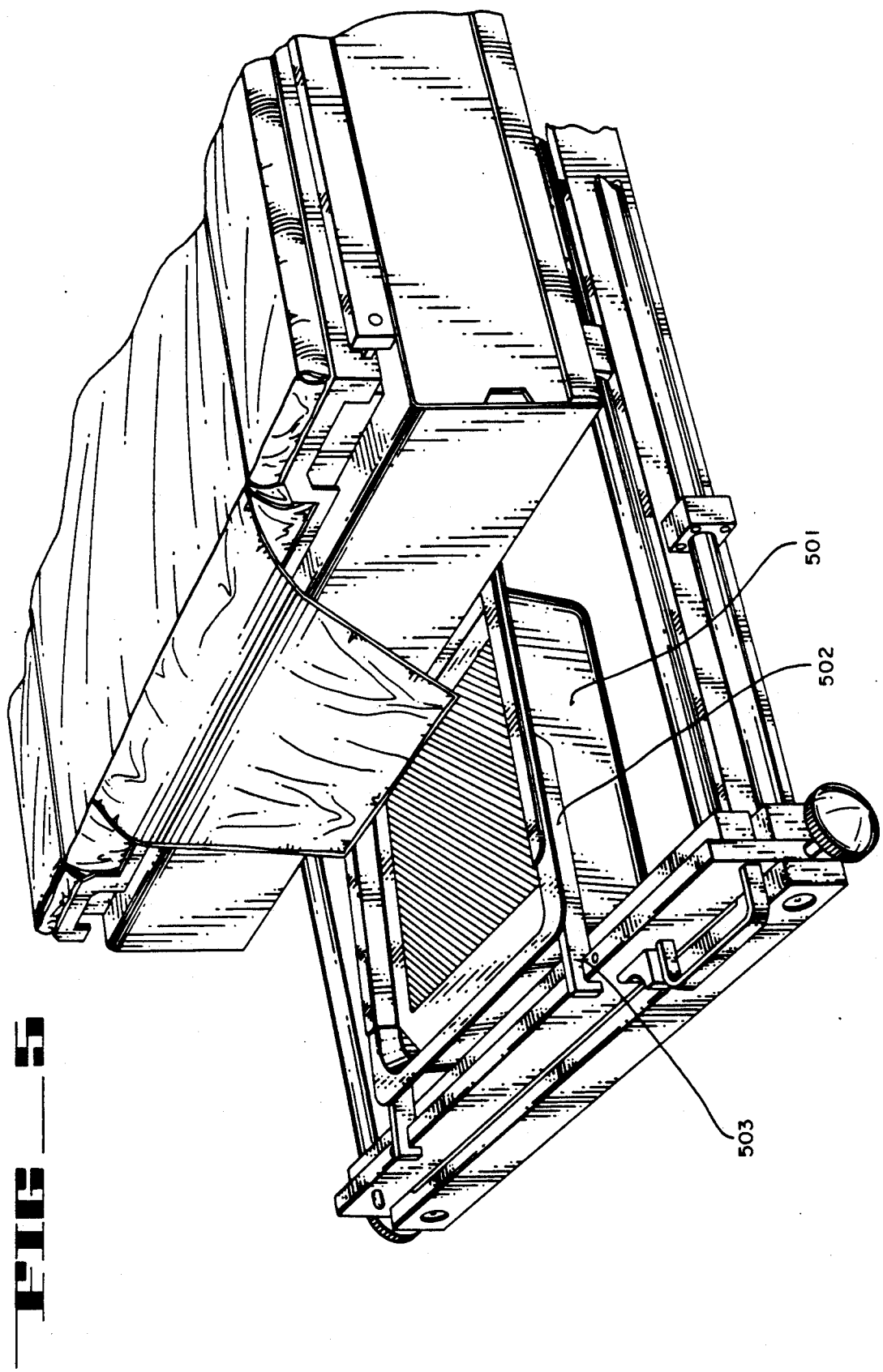
FIG_5

DRAIN BAG APPARATUS

BACKGROUND OF THE INVENTION

1. Field of the Invention

This invention relates to drain bag assemblies that attach to a diagnostic urology table.

2. Prior Art

In the field of urology, a urologist will often perform an examination or other medical procedure while a patient is lying or sitting on a specially designed diagnostic urology table. An example of such a diagnostic urology table is the UROVIEW 2000 manufactured and sold by OEC-DIASONICS, Inc. of Salt Lake City, Utah. During an examination or medical procedure, the patient will often excrete waste fluids. Depending on the nature of the examination or medical procedure, such waste fluids may be disposed of or collected for further analysis. The accumulation of such waste fluids is usually done with a drain bag or drain pan assembly that is attached to the diagnostic urology table. The use of a drain pan rather than a drain bag is generally at the preference of the urologist. Certain procedures may dictate the use of one of these devices to the exclusion of the other.

Typically, drain bag or drain pan assemblies are located at the perineal end of the diagnostic urology table directly between the urologist and the patient. Drain bag assemblies are designed to create a minimum of obstruction to the urologist. A drain bag assembly primarily comprises a drain bag, a support mechanism to hold the drain bag in place, a tube attached to the bottom of the drain through which the fluids are removed from the bag and attachment means for attaching the drain bag assembly to the diagnostic urology table.

Weickgenannt, U.S. Pat. No. 4,936,836 discloses a drain bag assembly with pivotally interconnected parts that is removably coupled to a urological table. The pivotally interconnected parts of the Weickgennant patent allow a urologist to varyingly distort the configuration of the frame in a horizontal direction. However, once the urologist removes pressure from the frame, the frame reverts back to it's original configuration. This may become cumbersome to the urologist particularly if the medical procedure being performed requires continual removal of pressure from the frame assembly, e.g. to pick up instruments. It would be desirable for a drain bag assembly whose configuration could be dynamically distorted, while at other times be fixed into a position selected by the urologist.

The Weickgenannt reference, like known drain bag assembly designs require removal of the assembly if a drain pan is to be used. Conversely, if a drain bag is to be used, a drain pan assembly would have to be removed. In order to avoid the requirement of removing and attaching drain bag/pan assemblies, it would be desirable for an assembly to be non-removably coupled to the diagnostic urology table that could accommodate either a drain pan or drain bag.

It is an object of the present invention to provide a drain bag support assembly that is non-removably coupled to a urological table and accommodates a drain pan or drain bag and further allows for fixing the assembly in a position selected by the urologist.

SUMMARY OF THE INVENTION

A drain bag support assembly that is non-removably coupled to a diagnostic urology table is disclosed. The drain bag support assembly provides a shock mechanism for allowing the urologist to dynamically collapse and shorten the assembly by exerting a horizontal force and a locking mechanism to fix the drain bag assembly into a closed or semi-closed position.

The assembly is comprised of a front support coupled to a rear support. The front support provides a stable surface for the urologist to exert horizontal pressure to collapse the assembly during an examination or other medical procedure and for fastening a front drain bag attachment bar. The front support is rigid in the vertical directions and prevents the accidental dislocation of the drain bag assembly that may result from upward pressure at some point on the front support. The rear support provides for attachment of the drain bag support assembly to the diagnostic urology table and the fastening of a rear drain bag attachment bar. A drain bag is fastened to the front and rear drain bag attachment bars.

The present invention further discloses a drain bag support assembly that can be fixed in a position away from the diagnostic urology table that allows for the use of other apparatus of the diagnostic urology tables or fixed in a position where the assembly is stored underneath the diagnostic urology table. Additionally, the drain bag assembly further provides for the fastening of a drain pan without requiring the removal of the drain bag assembly.

BRIEF DESCRIPTION OF THE DRAWINGS

FIG. 1 is a detailed illustration of the preferred embodiment of the present invention showing the drain bag assembly coupled to a urology table and in an open position.

FIG. 2a is a front view of a rear support as utilized by the present invention.

FIG. 2b is a back view of the rear support as utilized by the present invention.

FIG. 3a is a front view of a front support as utilized by the present invention.

FIG. 3b illustrates a front drain bag attachment bar coupled to a flexible pad support and a flexible pad as may be utilized by the present invention.

FIG. 4 is a side view of the shock mechanism and extension rods coupled to a diagnostic urology table as may be utilized by the present invention.

FIG. 5 is a front view of a drain pan attached to the drain bag assembly as may be utilized by the present invention.

DETAILED DESCRIPTION OF THE PREFERRED EMBODIMENT

An improved drain bag support assembly is disclosed. In the following description, numerous specific details e.g. fastening means, are set forth to provide a thorough understanding of the present invention. It will be obvious to one skilled in the art that the invention may be employed without these specific details. In other instances, well-known structures have not been set forth in order not to unnecessarily obscure the present invention.

The preferred embodiment of the present invention is illustrated in FIG. 1. A drain bag support assembly is permanently coupled to a diagnostic urology table 1. It should be noted that in this context, the terms permanently and non-removably coupled are used interchangeably. Both terms are used to describe the feature of the preferred embodiment that the drain bag support assembly is not removed from the diagnostic urology table 1 during normal, day-to-day operation. The drain bag assembly may preferably be removed for such functions as repair of the assembly by removal of bolts or similar attachment means. It is beneficial that the drain bag support assembly is permanently coupled to the diagnostic urology table 1 for at least two reasons. First, the need for maintaining a sterile storage location for the entire assembly is minimized (space for a flexible pad 13, front and rear attachment bars and a drain pan when not in use is still needed) since the drain bag assembly may be placed in a position where it is completely under the diagnostic urology table 1. Second, it is more convenient for the urologist to be able to use either a drain pan or a drain bag without having to undertake the removal of the undesired assembly and the attachment of the desired assembly. This is particularly important since it provides the urologist with the added flexibility of being able to easily switch the drain device being used while a medical procedure is being performed.

The major components of the drain bag support assembly are: a rear support 2, a rear drain bag attachment bar 3, a front support 4, a front drain bag attachment bar 5, a drain bag 6, a drain tube 7, exposed rods 9 coupled with shock mechanism 8, a locking mechanism 10 coupled with locking knobs 11 and extension support rods 12.

Coupled to the front support 4, is a flexible pad support 16 (discussed in more detail below) and a flexible pad 13. The flexible pad 13 provides a cushioned surface at which the urologist can exert horizontal pressure to move the drain bag assembly into a closed or semi-closed position. In the preferred embodiment, the flexible pad 13 is constructed of vinyl coated foam on a metal frame and defines a semi-circular shape on the side facing the urologist. It would be obvious to one skilled in the art that alternate shapes, e.g. a rectangular block, could be embodied without departing from the spirt and scope of the present invention.

When in typical use, the urologist will be positioned facing the drain bag assembly and the patient. The diagnostic urology table 1 is designed so that as fluids are emitted, they will either drop directly into the drain bag 6 or they will be guided by the shape of the diagnostic urology table 1 into the drain bag 6. The drain tube 7 coupled to the bottom of the drain bag 6 provides a means by which the drain bag 6 can be emptied without requiring the removal of the drain bag 6 from the assembly.

During the course of a medical procedure, the urologist may be required to move closer to the patient. In these situations, the drain bag assembly may become an obstruction. The drain bag assembly of the present invention addresses this problem by providing two means by which the distance the drain bag assembly extends from the back of diagnostic urology table 1 can be shortened.

The first means means involves locking the shock mechanism 8, so that the assembly is fixed in a closed or semi-closed position. The locking of the shock mechanism 8 refers to disabling the shock mechanism such that the drain bag assembly cannot be horizontally shortened using the means described below. The locking mechanism 10 used to lock the shock mechanism 8 is also discussed in greater detail below. To fix in a closed position, a horizontal force is placed on the front support 4 as described above until the extended rods 9 of the shock mechanism 8 are fully retracted, at which point the shock mechanism is locked. In the closed position the front support 4 will be positioned flush with the face of rear support 2.

To fix in a semi-closed position, the urologist exerts horizontal pressure to the front support 4 as described above, until the desired length is reached. The shock mechanism is then locked. A urologist may find a semi-closed position desirable when a horizontally shorter fixed position is required.

The second means requires that the the urologist exert horizontal pressure on the front support 4 towards the diagnostic urology table 1. This exertion of horizontal pressure causes the exposed rods 9 of shock mechanism 8 to retract into the shock mechanism 8 resulting in a shortening of the drain bag assembly in a horizontal direction with respect to the table, and a closing of the drain bag opening. This horizontal pressure can be exerted by the urologist pushing forward with his/her hands or torso. When unlocked, the shock mechanism 8 provides a resistive horizontal force in the opposite direction of the force applied by the urologist. When the urologist releases pressure against the front support 4, for example by moving away from the table, a spring within the shock mechanism 8 causes the exposed rods 9 to extend back to their original position. This results in the drain bag assembly reverting back to it's fully open position. The horizontal resistive pressure allows the assembly to remain rigid in the horizontal direction. In the preferred embodiment the exposed rods measure 14" in their fully open position. The exposed rods are constructed of stainless steel and have an outer diameter of 1".

In the preferred embodiment the shock mechanism 8 is a spring shock, but it would be obvious to one skilled in the art that alternative shock mechanisms, e.g. gas shocks, could be utilized without departing from the spirit and scope of the present invention. It should also be noted that varying spring tensions could be employed for the spring in the preferred embodiment. Thus, by replacement of the spring of the shock mechanism 8, or through the use of an adjustable spring arrangement, the amount of force required to move the drain bag assembly could be altered.

The locking mechanism 10 provides for fixing the drain bag assembly into a closed or semi-closed position. As described above, the locking mechanism 10 acts to disable the shock mechanism 8. To lock, the locking knobs 11 are turned in a clockwise fashion until tight. To return to a fully open position or to alter to a semi-closed position, the locking knobs 11 are turned in a counter-clockwise fashion until the shock mechanism 8 begins to push the front support horizontally outward. Although threaded knobs are utilized in the preferred embodiment, it would be obvious to one skilled in the art that alternative means of locking the shock mechanism 8, e.g. a latch, could be utilized without departing from the spirit and scope of the present invention.

The drain bag 6 is coupled to the drain bag assembly by the rear drain bag attachment bar 3 and the front drain bag attachment bar 5. The drain bag 6 defines sleeves into which the rear drain bag attachment bar 3 and the front drain bar attachment bar 5 are placed. When attached to the rear drain bag attachment bar 3 and the front drain bag attachment bar 5, the drain bag 6 is held in an open position. In the preferred embodiment, the front drain bag attachment bar 5 may be adjusted in the vertical direction to vary the height at which the drain bag 6 will sit in relation to the diagnostic urology table 1. The means for adjusting the height is discussed below with respect to the front support 4. When in a raised position, the drain bag 6 acts as a splash guard for the urologist. Further, height adjustment permits the urologist to locate the height of the drain bag 6 and the flexible pad 13 to their personal preference. It would be obvious to one skilled in the art to utilize a different means to attach a drain bag to the assembly, e.g. using clips, without departing from the spirit and scope of the present invention. The drain bag 6 in it's fully extended position, provides an opening with the dimensions 12"×14". The drain bag 6 is constructed of clear vinyl.

The drain bag assembly may also be extended away from the diagnostic urology table 1. This is accomplished by sliding a latch 14 located on the rear support 2 from a first locked position to a second unlocked position, and then pulling the rear support 2 outwards with handle 15. The latch 14 is coupled to a linkage assembly (not illustrated) The linkage assembly traverses the length of one of the extension support rods 12 and is further coupled to a pin. As will be described in more detail below, the extension support rod 12 and the linkage are positioned through a tubular sleeve 405 (illustrated in FIG. 4). The tubular sleeve 405 defines a plurality of holes, each of which represents a distance that the drain bag assembly may be extended. When in an unextended position, the pin extends through one of such holes defined by the tubular sleeve 405. When the pin extends through a hole defined by the tubular sleeve 405, the assembly is horizontally rigid.

When the latch 14 is moved to the second position, the linkage causes the pin to be removed from one of the holes defined by tubular sleeve 405. When the latch 14 is released to the first closed position, the pin is projected perpendicularly towards the outer surface of the tubular sleeve 405 towards one of the holes defined by the tubular sleeve 405. As the drain bag assembly is pulled outwards, the extension support rods 12 are extended outwards and the pin will insert into one of the holes defined by the tubular sleeve 405. The extension support rods 12 provide horizontal and vertical rigidity for the drain bag assembly when it is moved to this position. In a fully extended position, the drain bag assembly can be positioned 16" from the diagnostic urology table 1.

FIG. 2a illustrates in a front view of rear support 2. The rear support 2 is constructed of stainless steel. The rear support 2 is 25" in length 4" in height and is 0.5" thick. The rear support 2 defines a cutout 201 along it's bottom side. The cutout 201 is 2" from each side and is 2" in height. The cutout 201 results in the rear support 2 being in the shape of the bottom of the letter "H" and defining bottom legs 202. In the preferred embodiment the bottom legs 202 of the rear support are square shaped with the dimensions of 2"×2".

Within the bottom legs 202, holes 203 are defined. The holes 203 have a diameter of 1.045". When assembled, exposed rods 9 of the shock absorbing mechanism 8 extend through each of the holes 203. Further defined within each of the bottom legs 202 are four (4) screw holes 204 for coupling a shock support block 205. Rear support 2 also defines a pair of threaded holes 206 along the side edges, through which a screw neck of the locking knob 11 is extended. The diameter of each of the threaded holes 206 is ⅜".

The top edge of the rear support 2 defines two (2) holes 211 through which the rear drain bag attachment bar 3 is coupled. As illustrated in FIG. 2a, the rear drain bag attachment bar 3 defines a top rail 207 which is substantially parallel to the top of the rear support 2. The length of the top rail 207 is 13.69". A first curved 90 degree bend 208 is located 2" inches from the bottom of the rear support 2. The bend 208 is directed horizontally outward away from the urology table 1. A second curved 90 degree bend upwards 209 is located 2.00" from the first bend 208. The rod then extends upward 4.5" until it defines the top rail 207.

In the preferred embodiment, the rear drain bag attachment bar 3 is removable and is constructed of stainless steel. It would be obvious to one skilled in the art to design a rear drain bag attachment bar 3 that is not removable, that would define a different shape or that is constructed of a different material may be substituted without departure from certain aspects of the present invention. However, with respect to other advantages shown by the present invention, it is important that bar 3 may be removed as an obstruction. For example it is sometimes desirable to couple a drain pan with the diagnostic urology table 1. In the preferred embodiment, the bar 3 must be removed to allow coupling of such a pan. However, alternate embodiments can be envisioned in which the pan may be coupled with and supported by the bar 3.

Also defined on the rear support 2, is the slide switch 14 and the handle 15. As described earlier, the slide switch 14 and the handle 15 are used to extend the entire drain bag assembly in a horizontal direction away from the urology table 1. The slide switch 14 is constructed of stainless steel and is located approximately 19.5" from the left edge of the rear support 2 and 1.25" from the top of rear support 2. The handle 15 is located on the right side of the rear support 2. The handle 15 projects 1.5" from the face of the rear support 2 and is 4" long. The handle 15 is fastened to the rear support 2 by two #10-32 screws. It should be noted that the location of the slide switch 14 and the handle 15 is significant because the assembly may be extended even when the drain bag is attached. This location allows access to slide switch 14 and the handle 15 when the drain bag is attached.

FIG. 2b illustrates the back side of rear support 2. The latch linkage cover 210 is coupled to the back side of the rear support 2. This cover 210 has dimensions 24.5"×1"×1" and defines receiving holes 212 for the extension rods 12. The cover 210 is fastened to the rear support by four 6-32 screws. The rear support 2 is coupled to the extension support rods 12. The extension support rods 12 extend lengthwise coupled to the underside of the diagnostic urology table 1. The extension support rods 12 are discussed in more detail below.

Shock support block 205 has the dimensions 2"×2"×1" and is of substantially the same height and width as the bottom legs 202. Shock support block 205 defines screw receiving holes (not illustrated) and a hole 213 (illustrated in FIG. 2b) through which the exposed rods 9 of the shock absorbing mechanism 8 extends. The shock support block 205 is fastened to the rear support 2 using four #10-32 screws. The shock mounting block 205 provides horizontal and vertical stability and rigidity for the shock absorbing mechanism 8 when it is assembled with the diagnostic urology table 1.

Referring now to FIG. 3a, the front support 4 is substantially rectangular in shape and has the dimensions 25"×2"×0.625". The front support 4 is constructed of stainless steel. It would be obvious to one skilled in the art that construction of front support 4 could be accomplished with other materials and would not depart from the spirit and scope of the present invention.

The top of the front support 4 defines two holes 301, through which the flexible pad support 16 is coupled to the front support 4. The diameter of the holes 301 are 0.26". The back-side of the front support 4 defines receiving holes (not illustrated) for the ends of the exposed rods 9 of the shock mechanism 8. The front side of the front support 4 defines holes 303 through which screws are extended in order to fasten the exposed rods 9.

Referring to FIG. 3b, the flexible pad 13 is fastened to the flexible pad support 16. Flexible pad 13 is formed in a manner to cover the front and edges of the front support 4. The flexible pad 13 is fastened to the flexible pad support 16 with velcro. The flexible pad support 13 is comprised of a flexible pad support surface 304, attachment bar holders 305, mounting pins 306, fastening brackets 307 and a vertical plane surface 308. The flexible pad support surface 304 and the vertical plane surface 308 are made of stainless steel and fastened together by a soldering process. The flexible pad support surface 304 rests on the inside of the flexible pad 13 and is of the same shape as the flexible pad 13. The flexible pad support surface 304 provides rigidity to the flexible pad 13 when pressure is applied, e.g. when horizontal force is being exerted on the drain bag assembly is being to shorten it.

The vertical plane surface 308 provides a surface to fasten the fastening brackets 307 to the flexible pad support 16. The dimensions of the vertical plane surface 308 are 20.88"×2.50". The fastening brackets 307 are fastened to the vertical plane surface 308 by a welding process. As illustrated in FIG. 3b, attachment bar holders 305 are welded to the fastening brackets 307. The attachment bar holders 305 are welded to the fastening brackets 307 by 0.312" (I.D.) ×1.50" tube. When assembled, the front drain bag attachment bar 5 is coupled to the attachment bar holders 305 of the flexible pad support 16. The mounting pins 306 are welded to the flexible pad surface 304 and extend through a hole defined by the fastening bracket 307. The fastening bracket 307 provides alignment and horizontal rigidity for the mounting pins 306 when they are inserted into the holes 301 of the front support 4.

FIG. 4 is a side view of the shock mechanism 8 and extension support rods 12 as coupled to the diagnostic urology table 1 of the preferred embodiment. It should be noted that the opposite side view of the drain bag assembly will be a mirror image to that illustrated in FIG. 4, with the exception of the linkage assembly. In the preferred embodiment, the linkage assembly extends down only one of the extension support rods 12. The choice of which side the linkage assembly is installed is dependant on the particular configuration of the accompanying urology table 1. In any event, the extension support rods 12 are fastened to the rear support 2 and to the urology table 1. The extension support rods 12 are fastened to the urology table 1 through mounting blocks 403 and 406. The connection bars 401 are fastened to shock support block 205 and slide bushing blocks 404. The dimensions of the connection bar 401 are 25.5"×2"×0.25".

The extension rod 12 extends through holes (not illustrated) defined by each of the mounting blocks 403 and 406. The mounting blocks 403 and 406 are coupled to urology table 1 via spacers 403a and 406a, respectively, and fastened with four ¼-20 screws (per block). At the end of the extension support rod 12, a cap 408 is defined. The cap 408 is of a diameter 1.375" which is large enough to prevent it from going through the hole defined by mounting block 406. This prevents the extension support rod 12 from becoming over-extended causing the drain bag assembly to be de-coupled from the urology table 1.

Located between mounting blocks 403 and 406 is the tubular sleeve 405. The extension support rods 12 extend through the tubular sleeve 405. The tubular sleeve 405 is of the length 22.50" and has an outer diameter of 1.375". On the side of the tubular sleeve 405 facing the urology table are defined a plurality of holes 410. In the preferred embodiment 0.375 DIA holes are defined. The holes are evenly spaced on the tubular sleeve 405 along a center line. The plurality of holes 410 are used by the linkage assembly, as described above, to set the extension rods into a fixed position. The pin mechanism (not illustrated) of the linkage assembly is housed in the extension support rod 12. Slide Bushing block 404 traverses across the surface of the tubular sleeve 405 as the extension support rods 12 are being move into a desired position. The slide bushing blocks 404 are assembled over the tubular sleeve 405 and fastened to the connection bar 401 as a support function.

As described above, the shock mounting block 205 provides stability for the shock mechanism 8. Also coupled to the shock mechanism 8 is a stop block 402. The stop block 402 is coupled to the outer tube of the shock mechanism 8 and acts to prevent the inadvertent over extension of the shock mechanism. The dimensions of the stop block 402 are 2"×1.48"×1". The shock mechanism 8 further comprises a compression rod 409. The compression rod 409 provides a means for the resistive horizontal pressure needed when the shock absorption mechanism 8 is in operation. The compression rod 409 is coupled to a metal ball stud 411 using a ball socket 412. When the ball socket 412 is removed from the metal strap 411, the shock absorption mechanism becomes inoperative. It is desirable to cause the shock absorption mechanism 8 to become inoperative when the drain bag assembly is not being used and is being stored under the urology table 1.

FIG. 5 illustrates a drain pan 501 attached to the drain bag assembly. Coupled to each side of the drain pan 501 is a fastening arm 502. Each end of the fastening arm 502 defines a notch 503. Each fastening arm 502 is fastened to the drain pan 502 through a welding process. To attach a drain pan 501, the rear drain bag attachment bar 3, the front drain bag attachment bar 5 and the flexible pad support 16 are removed and the drain bag assembly is put into a closed position as described above. The assembly is then extended away from the table, by moving the latch 14 into the second open position and pulling horizontally on the handle 15. As described above the mounting of the latch 14 into the second open position causes a pin in the linkage to disengage from a hole define by sleeve 405. The assembly is then pulled out to a pre-determined length so that the drain pan 501 can be fastened. At this point the pin will engage into one of the holes defined by sleeve 405, thus providing horizontal rigidity to the assembly.

The notches 503 of the arms 502 are then placed in a position of alignment with the rear support 2. The weight of the drain pan 501 causes the notches 503 to fasten securely with the rear support.

Thus an improved drain bag assembly is disclosed. By providing for the assembly to collapse and be locked into a desired position, a urologist can customize the assembly to their needs. Further, since the assembly is non-removable and can fasten a drain pan, the need for removal of the entire drain bag assembly when a drain pan is desired is eliminated.

We claim:

1. An assembly for supporting a drain bag in combination with a urology table, said assembly coupled to said urology table, said assembly comprised of:
   a first support means for supporting a front portion of said drain bag;
   a second support means for supporting a rear portion of said drain bag; and
   horizontal movement means for allowing horizontal movement of said assembly relative to said urology table, said horizontal movement means non-removably coupled to said urology table.

2. The assembly as recited by claim 1, wherein said first support means for supporting a front portion of the drain bag is comprised of a fastening rod coupled to a front support plate.

3. The assembly as recited by claim 2, wherein said horizontal movement means is comprised of:
   a shock mechanism; and
   one or more shock arms, said shock arms fastened to said front support plate, said shock arms collapse into said shock mechanism when a horizontal force is applied to said front support plate and return to a fully extended position when said horizontal force is released.

4. The assembly as recited by claim 3, wherein said horizontal movement means is further comprised of a locking means for disabling said shock mechanism.

5. The assembly as recited by claim 4, further comprising attachment means for attaching a drain pan.

6. A urology table including a drain assembly non-removably coupled with said table; said drain assembly including:
   support means for supporting a first drain device and a second drain device; and
   horizontal movement means for allowing horizontal movement of said support means relative to said urology table.

7. The drain assembly as recited in claim 6, wherein said first drain device is a drain bag.

8. The drain assembly as recited in claim 7, wherein said support means is comprised of:
   a front support plate coupled to a front fastening bar for supporting a front portion of said drain bag, said front support plate further coupled to said horizontal movement means; and
   a rear support plate coupled to a rear fastening bar for supporting a rear portion of the drain bag, said rear support plate coupled to said urologic table.

9. The assembly as recited in claim 7, wherein said horizontal movement means is comprised of:
   a shock absorbing mechanism;
   means for locking said shocking absorbing mechanism into a closed position or a semi-closed position; and
   means for extending said assembly in a plurality of positions that are a pre-determined horizontal distance from said urology table.

10. The assembly as recited in claim 8, wherein said second drain device is a drain pan.

11. The assembly as recited in claim 9, wherein said shocking absorbing mechanism is in a closed position and said assembly is in an associated one of said pre-determined horizontal distances from said urology table, when said drain pan is fastened.

12. An assembly for supporting a drain device, said drain device non-removably coupled to a urology table, said assembly comprised of:
   a front support means for supporting a first drain device;
   a rear support means for supporting the first drain device and a second drain device;
   a first horizontal movement means coupled to said front support means for allowing dynamic horizontal movement of said first drain device relative to the rest of the assembly; and
   a second horizontal movement means for horizontal movement of said assembly relative to said urology table.

13. The assembly as recited in claim 12, wherein said first drain device is a drain bag.

14. The assembly as recited in claim 13, wherein said first horizontal movement means is a shock absorption mechanism capable of being in open, closed, or semi-closed positions.

15. The assembly as recited in claim 12, wherein said second horizontal movement means is further comprised of linkage means for fixing said assembly into a plurality of positions.

* * * * *